US00PP33421P2

(12) United States Plant Patent
Moucheboeuf

(10) Patent No.: US PP33,421 P2
(45) Date of Patent: Aug. 31, 2021

(54) ***DIANTHUS* PLANT NAMED 'WP20 PPA01'**

(50) Latin Name: ***Dianthus* x *hybrida***
Varietal Denomination: WP20 PPA01

(71) Applicant: Plant Genetics International Ltd., Exeter (GB)

(72) Inventor: Laetitia Moucheboeuf, Dawlish (GB)

(73) Assignee: PLANT GENETICS INTERNATIONAL, LTD., Exeter (GB)

( * ) Notice: Subject to any disclaimer, the term of this patent is extended or adjusted under 35 U.S.C. 154(b) by 0 days.

(21) Appl. No.: 17/122,112

(22) Filed: Dec. 15, 2020

(51) Int. Cl.
*A01H 5/02* (2018.01)
*A01H 6/30* (2018.01)

(52) U.S. Cl.
USPC ..... Plt./283

(58) Field of Classification Search
USPC ..... Plt./263.1, 272, 283
See application file for complete search history.

*Primary Examiner* — Susan McCormick Ewoldt
*Assistant Examiner* — Karen M Redden
(74) *Attorney, Agent, or Firm* — Weatherly IP Solutions, LLC; Barbara Campbell

(57) ABSTRACT

A new cultivar of *Dianthus* plant named 'WP20 PPA01' that is characterized by a compact mounding habit with glaucous blue-green foliage, single bright crimson flowers with a darker crimson band, blooming from May through October, and suitable for use as a flowering plant in pots and containers, is disclosed.

2 Drawing Sheets

Genus and species: *Dianthus* x *hybrida*.
Variety denomination: 'WP20 PPA01'.

BACKGROUND OF THE NEW PLANT

The present invention relates to a new and distinct cultivar of hardy *Dianthus*, commonly known as Alpine Pink, which is grown for use as a flowering plant for pots and containers and for planting in the garden and landscape. The new cultivar is known botanically as *Dianthus* x *hybrida* and will be referred to hereinafter by the cultivar name 'WP20 PPA01'.

'WP20 PPA01' is a complex hybrid plant that is the product of a long-term breeding program conducted in a cultivated area of Ashcombe Road, Dawlish, Devon, United Kingdom. 'WP20 PPA01' was selected in 2012 for its single bright crimson flowers and glaucous blue- green foliage.

'WP20 PPA01' arose and was selected as a seedling which resulted from the open pollination of a prior selection of *Dianthus*. The male parent is an unknown and unnamed *Dianthus* and the female parent is the *Dianthus* code name 'IVA 05.01' (unpatented and unreleased). The female parent was grown within the inventor's stock of breeding lines.

Asexual reproduction of 'WP20 PPA01' was first accomplished in 2012 in a cultivated area of Ashcombe, United Kingdom using the propagation method of shoot cuttings. 'WP20 PPA01' has been determined to be stable and reproduces true to type in successive generations of asexual propagation using shoot cuttings.

SUMMARY

The following traits have been repeatedly observed and represent the characteristics of the new *Dianthus* cultivar 'WP20 PPA01'. 'WP20 PPA01' has not been tested under all possible conditions and phenotypic differences may be observed with variations in environmental, climatic and cultural conditions, however, without any variance in genotype.

1. 'WP20 PPA01' exhibits a compact mounding habit.
2. 'WP20 PPA01' bears single bright crimson flowers.
3. The petals of 'WP20 PPA01' are flat.
4. 'WP20 PPA01' blooms from May through October.
5. The flowers of 'WP20 PPA01' exhibit a medium sweet fragrance.
6. 'WP20 PPA01' exhibits glaucous blue-green foliage.
7. At maturity, the height of the foliage mound of 'WP20 PPA01' is 20 cm, and the width is 30 cm.
8. 'WP20 PPA01' is perennial and is hardy at least to minus 15° Centigrade.
9. 'WP20 PPA01' is suitable for use as a flowering plant in pots and containers, and for use as a cut flower and in bouquets.

BRIEF DESCRIPTION OF THE PHOTOGRAPHS

The accompanying color photographs illustrate the overall appearance of the new *Dianthus* variety 'WP20 PPA01' showing colors as true as it is reasonably possible to obtain in colored reproductions of this type. Colors in the photographs may differ from the color values cited in the detailed botanical description, which accurately describe the actual colors of the new variety 'WP20 PPA01'.

Figure 1:
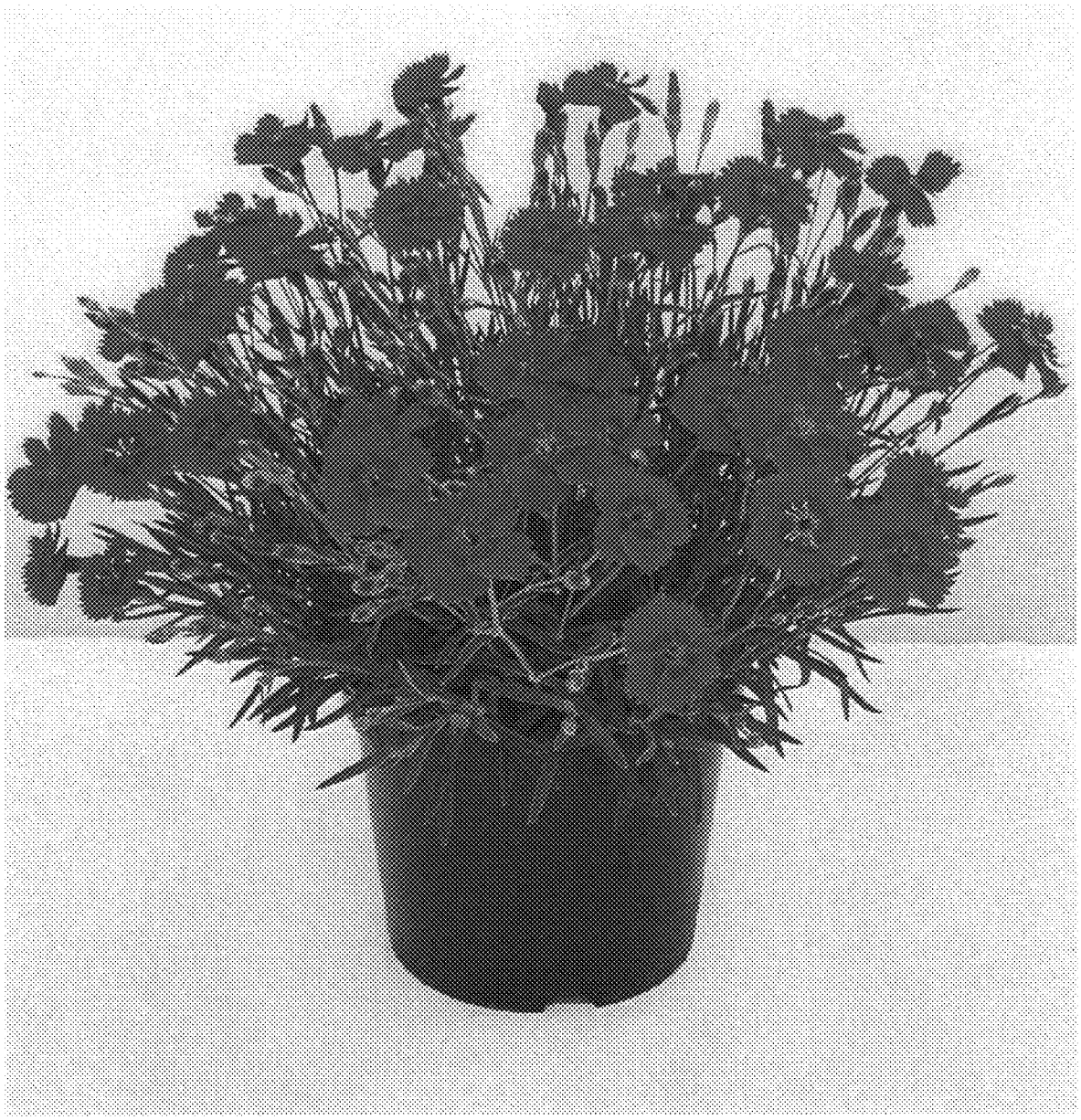
FIG. 1 depicts an entire flowering plant of 'WP20 PPA01'.
Figure 2:
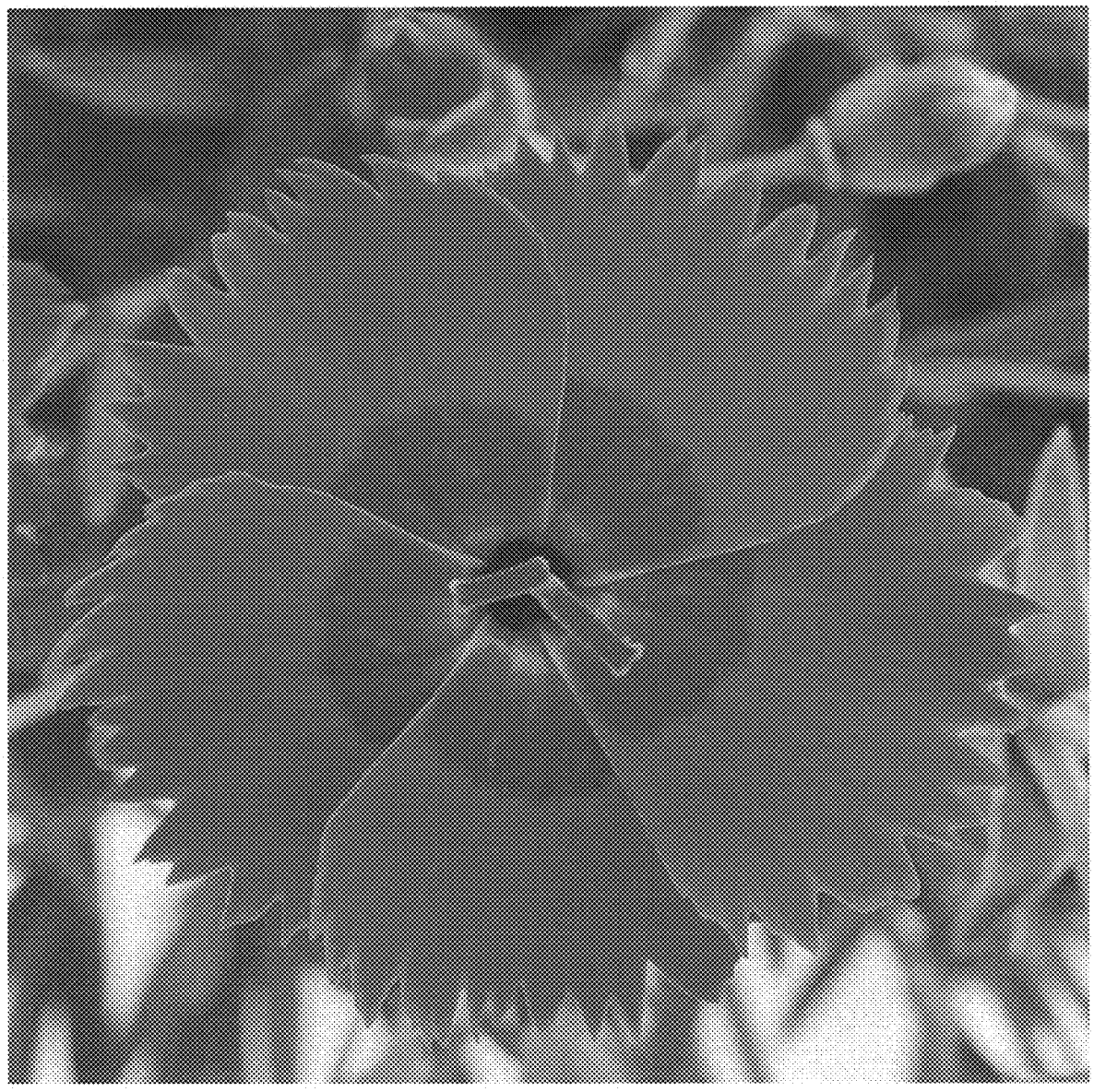
FIG. 2 depicts a close-up view of the flower of 'WP20 PPA01'.

Photographs were taken in May 2020 in Dawlish, Devon, United Kingdom, on ten-month old plants which have been grown outdoors in 3-liter containers. No chemicals were used to treat the plants. All photographs were made using conventional techniques and although colors may appear different from actual colors due to light reflectance they are as accurate as possible by conventional photography.

BOTANICAL DESCRIPTION OF THE PLANT

The following is a detailed description of the new cultivar 'WP20 PPA01'. Data was collected from plants grown in 3-liter containers under an unheated glasshouse in Ashcombe, Dawlish, United Kingdom. The color determinations are in accordance with the sixth edition (2015) of The Royal Horticultural Society Colour Chart of The Royal Horticultural Society, London, England, except where general color terms of ordinary dictionary significance are used. No chemicals were used to treat the plants. Growing conditions are typical to other *Dianthus*.

Botanical classification: *Dianthus*.

*Variety*.—'WP20 PPA01'.

*Species*.—X *hybrida*.

*Common names*.—Hybrid *Dianthus*, Alpine Pink.

*Commercial classification*.—Hardy perennial.

*Use*.—Ornamental plant for pots and containers.

Parentage: 'WP20 PPA01' is a hybrid plant that resulted from the open pollination of *Dianthus* x *hybrida* plants.

*Female parent plant*.—'PPA 05.01' experimental *Dianthus* plant (unpatented).

*Male parent plant*.—Unknown.

Plant description:

*Bloom period*.—May to October.

*Plant habit*.—Compact mounding habit.

*Plant height*.—20 cm in overall height, including flower canopy.

*Plant width*.—30 cm in width.

*Plant hardiness*.—Hardy to minus 15° Centigrade.

*Type*.—Perennial.

*Root system*.—Fibrous.

*Propagation*.—Propagation is accomplished using shoot cuttings.

*Cultural requirements*.—Plant in full sun, well-drained and moderately fertile soil and keep well fertilized and watered.

*Time required to produce a rooted cutting*.—5 weeks are needed to produce a rooted cutting.

*Temperature recommended for cuttings to produce roots*.—The air temperature needed is a minimum of 15° Centigrade air temperature and base heat of 21° Centigrade.

*Crop time*.—6 to 9 months is needed to produce a finished 3-litre container size from a well-rooted cutting.

Stem:

*Shape*.—Cylindrical, solid.

*Dimensions*.—7 cm in length, 3 mm diameter.

*Surface*.—Glabrous and glaucous.

*Color*.—145B, 145C and 145D (in the sheathing zone).

*Branching*.—Numerous shoots from the axils of the lower leaves.

*Internode length*.—1 to 2 mm between nodes (before extension of peduncle).

*Node dimensions*.—3 mm in diameter and 2 mm in length.

Leaf:

*Type*.—Evergreen.

*Dimensions*.—6 cm in length, 3 mm in width.

*Color adaxial surface*.—133A.

*Color abaxial surface*.—N189B.

*Shape*.—Linear.

*Division*.—Simple.

*Apex*.—Acute.

*Base*.—Decurrent.

*Venation*.—Absent on the adaxial surface and only one central vein visible on the abaxial surface.

*Margins*.—Entire.

*Attachment*.—Sheathing.

*Arrangement*.—Opposite and spiraling up stem.

*Surfaces* (*adaxial and abaxial*).—Glaucous.

*Fragrance*.—Absent.

Flowers:

*Inflorescence*.—Simple cyme.

*Type*.—Single, polypetalous.

*Number*.—2 per stem.

*Dimensions* (*including calyx*).—25 mm in length and 42 mm in diameter.

*Shape*.—Circular.

*Lastingness*.—10 days at 20° Celsius on the plant; 8 to 10 days off the plant.

*Fragrance*.—Medium, sweet.

*Flowering period*.—May to October.

Peduncle:

*Shape*.—Cylindrical, solid.

*Dimensions*.—15 cm in length, 2 mm in diameter.

*Surface*.—Glabrous, moderately waxy.

*Strength*.—Strong, rigid.

*Color*.—122A.

Bud:

*Shape*.—Cylindrical.

*Color*.—N138A to N138B on apical half and 144A to 144B on basal half (below the bracts).

*Anthocyanin*.—Present.

*Dimensions*.—14 mm in length and 4 mm in width.

Petals:

*Corolla*.—Upper and lower part of corolla is flat.

*Petal arrangement*.—Persistent, apopetalous and overlapping.

*Margin*.—Serrate.

*Indentations*.—Up to 3 mm deep.

*Texture*.—Soft.

*Type*.—Single.

*Number of petals*.—5.

*Dimensions*.—40 mm in length, 28 mm in width.

*Petal shape*.—Fan shape.

*Petal surface*.—Glabrous.

*Petal apex*.—Fan shaped, serrate.

*Petal base*.—Strap shaped, tapering towards base.

*Color pattern*.—Blade is crimson, with a medium width darker crimson band.

*Petal color* (*adaxial surface*).—Ground color of blade: 53B (nearest). Color of band: 53A (nearest). Band width: 6 mm. Color of middle of strap: 149C. Color of base of strap: 149D.

*Petal color* (*abaxial surface*).—Ground color of blade: 58A (nearest). Color of middle of strap: 149C.

*Color of base of strap*.—149D.

Calyx:

*Dimensions*.—18 mm in length and 7 mm in width.

*Shape*.—Cylindrical and straight.

*Sepals*.—5, fused up to 4 mm below the apex.

*Sepal dimensions*.—19 mm in length and 4 mm in width.

*Apex*.—Acute.

*Base*.—Truncate.

*Color of sepals, outer surface.*—N138B to N138C on apical half and 144A to 144B on basal half (below the bracts).

*Color of sepals, inner surface.*—138A on the apical half and 138B on the basal half.

*Anthocyanin.*—Present as a hue around the apex of the bracts and at the base of the calyx.

*Splitting.*—Not observed.

Epicalyx:

*Number of bracts.*—1 pair of 2.

*Bracts shape.*—Medium acuminate.

*Bracts dimensions.*—8 mm in length and 5 mm in width.

*Bracts color.*—N138A, N138B, 139C and 139D are all present.

*Anthocyanin.*—Present.

*Number of bracteoles.*—1 pair of 2.

*Bracteoles shape.*—Acute.

*Bracteoles dimensions.*—9 mm in length and 9 mm in width.

*Bracteoles color.*—N138A, N138B, 139C and 139D are all present.

*Bracteoles anthocyanin.*—Present.

Reproductive organs:

*Description.*—Plants polygamous, bearing flowers which are either perfect (male and female parts present) or a greater number of flowers which exhibit female parts only.

*Stamen number (where present).*—10.

*Stamen dimensions.*—About 25 mm in length and 0.5 mm in width.

*Color of filaments.*—Whiter than NN155A, becoming 70D at 4mm below and towards anthers. Anther number: 10.

*Anther dimensions.*—2 mm in length, 1 mm in diameter.

*Color of anthers.*—77D.

*Anther attachment.*—Dorsifixed.

*Pollen.*—Present.

*Style number.*—2.

*Style shape.*—Cylindrical, shoulder absent.

*Color of style.*—Whiter than NN155A.

*Style dimensions.*—15 mm in length and 1 mm in width.

*Stigma number.*—2 (one on each style).

*Stigma shape.*—Linear as extension to style, recurving, apex microscopically bifid.

*Stigma color.*—77A.

*Stigma dimensions.*—Each branch approximately 10 mm in length, 1.0 mm to 1.5 mm in diameter, fimbriated, protrudes approximately 6 mm above petal plane at maturity.

*Ovary position.*—Superior.

*Ovary dimensions.*—7 mm in length and 4 mm in diameter.

*Ovary shape.*—Spindle.

*Ovary surface and texture.*—Smooth.

*Ovary color.*—145A at the uppermost surface, becoming paler 145B at the lowest surface.

Seed:

*Color.*—202A.

*Length.*—4 mm.

*Diameter.*—3 mm.

*Shape.*—Oval and flattened.

*Surface.*—Crinkled.

*Number.*—Varies, up to 10 per pod.

Diseases and pests: Susceptible to known *Dianthus* pests and disease but no other susceptibilities to pests or disease are known.

COMPARISON WITH PARENTAL LINE AND KNOWN VARIETY

'WP20 PPA01' is distinguishable from the female parent as follows. The female parent 'IVA 05.01' bears smaller single flowers which are dark pink in color and petals with a medium pink to light pink picotee margins. In addition, in overall size, plants of 'IVA 05.01' are smaller than plants of 'WP20 PPA01'.

The variety of *Dianthus* considered to most closely resemble 'WP20 PPA01' is *Dianthus* Plant Named 'Red Dwarf' (U.S. Plant Pat. No. 14,437). In comparison with 'Red Dwarf', 'WP20 PPA01' bears more vibrant crimson flowers with a darker eye and of slightly larger diameter. The petal margins of 'WP20 PPA01' are more deeply serrated than the petal margins of 'Red Dwarf'. The overall flowering height of 'WP20 PPA01' is greater than the flowering height of 'Red Dwarf'. 'WP20 PPA01' is more floriferous than 'Red Dwarf'.

I claim:

1. A new and distinct cultivar of *Dianthus* plant named 'WP20 PPA01' as described and illustrated herein.

* * * * *